United States Patent [19]

Fahey, III et al.

[11] Patent Number: 5,145,676

[45] Date of Patent: Sep. 8, 1992

[54] METHOD AND AGENTS FOR PROMOTING WOUND HEALING

[75] Inventors: Thomas J. Fahey, III; Barbara A. Sherry, both of New York; Anthony Cerami, Shelter Island, all of N.Y.

[73] Assignee: The Rockefeller University, New York, N.Y.

[21] Appl. No.: 652,198

[22] Filed: Feb. 7, 1991

Related U.S. Application Data

[63] Continuation-in-part of Ser. No. 399,971, Sep. 1, 1989, which is a continuation-in-part of Ser. No. 240,078, Sep. 2, 1988, and Ser. No. 377,937, Jul. 10, 1989, and a continuation-in-part of Ser. No. 238,937, Sep. 2, 1988, each is a continuation-in-part of Ser. No. 104,827, Oct. 2, 1987, which is a continuation-in-part of Ser. No. 766,852, Aug. 16, 1985, which is a continuation-in-part of Ser. No. 414,098, Sep. 7, 1982, Pat. No. 4,603,106, which is a continuation-in-part of Ser. No. 351,290, Feb. 22, 1982, abandoned, which is a continuation-in-part of Ser. No. 299,932, Sep. 8, 1981, abandoned.

[51] Int. Cl.$^5$ .............................................. A61K 37/00
[52] U.S. Cl. .................................... 424/85.1; 514/12; 514/21
[58] Field of Search ................... 424/85.1; 514/12, 21

[56] References Cited

U.S. PATENT DOCUMENTS 4,603,106  7/1986  Ceremi et al. .................. 435/5

OTHER PUBLICATIONS

Deuel et al. PNAS, USA vol. 78, No. 7, pp. 4584–4587, Jul. 1981.

*Primary Examiner*—Merrell C. Cashion, Jr.
*Assistant Examiner*—Choon P. Koh
*Attorney, Agent, or Firm*—Klauber & Jackson

[57] ABSTRACT

The present invention relates to the treatment of wound healing dysfunction by the administration of one or more would healing modulators. The wound healing modulator may be selected from appropriate wound healing agents and binding partners, and particularly agents that enhance wound healing. The agent may comprise a cytokine, or mixture of cytokines that are also capable of binding to heparin, and inducing localized inflammation characterized by polymorphonuclear cell infiltration when administered subcutaneously. Particular agents comprise the inflammatory cytokines MIP-1, MIP-1α, MIP-1β and MIP-2. Diagnostic and therapeutic utilities are proposed, and pharmaceutical compositions are likewise set forth.

16 Claims, 4 Drawing Sheets

METHOD AND AGENTS FOR PROMOTING WOUND HEALING

The research leading to the present invention was funded in part by grants from the National Institutes of Health and the Rockefeller Foundation.

RELATED APPLICATIONS

The present application is a continuation-in-part of co-pending application Ser. No. 399,971 filed Sep. 1, 1989 which is a continuation-in-part of co-pending application Ser. No. 240,078, filed Sep. 2, 1988; and of co-pending application Ser. No. 377,937, filed Jul. 10, 1989, which is, in turn, a continuation-in-part of co-pending application Ser. Nos. 240,078 and 238,937 both filed Sep. 2, 1988, each of which is a continuation-in-part of Ser. No. 104,827, filed Oct. 2, 1987, which is in turn a continuation-in-part of Ser. No. 766,852, filed Aug. 16, 1985, which is in turn a continuation-in-part of Ser. No. 414,098, filed Sep. 7, 1982, now U.S. Pat. No. 4,603,106, issued Jul. 29, 1986, which is in turn a continuation-in-part of Ser. No. 351,290, filed Feb. 22, 1982, now abandoned, which is in turn a continuation-in-part of Ser. No. 299,932, filed Sep. 8, 1981, also abandoned. Applicants claim the benefit of these applications under 35 U.S.C. Section 120.

RELATED PUBLICATIONS

The Applicants are authors or co-authors of the following publications believed to be related to the subject matter of the present invention. [Applicants co-authored with K. T. Tracey, S. van Deventer, W. G. Jones II, J. P. Minei, S. Morgello and G. T. Shires] "Cytokine Production in a Model of Wound Healing: The Appearance of MIP-1, MIP-2, Cachectin/TNF and IL-1", *Cytokine*, 2(2):92-99 (1990).

BACKGROUND OF THE INVENTION

The present invention generally relates to the repair of damaged tissues in animals and particularly humans, and, more particularly, to the modulation of the healing of wounds in such tissue.

Injury to animal tissue resulting in tissue wounds occurs from an endless variety of pathological and non-pathological causes. In response to injury, a variety of cells have been determined to cooperate to repair the damaged tissue and heal the wound. Cells resident in the local tissue participate, as do circulating blood cells specifically recruited into the wound itself and the area nearby. Dramatic changes in cellular function are required by both the resident and recruited cells in order to initiate, coordinate, and sustain the complex process of wound healing. Damaged cells and disrupted tissue matrix must be removed, new cells must be born, and must grow and mature to replace those lost. The tissue matrix must be resynthesized and remodeled, and even the microvasculature may need to be rebuilt to supply the new tissue. It is now recognized that cytokines exchanged among responding cells mediate the induction, control, and coordination of these and other cellular functions necessary to successfully heal the wound.

Among recruited cells, macrophages are considered essential for normal wound healing. Macrophages are a rich source of peptide cytokines, which, as a group, are thought to be integral to the tissue repair responses to local injury. It is well known that individual cytokines can act on more than one cell type and can have more than one effect. New cytokines continue to be described, and new functions are being attributed to them, as well as to previously described cytokines.

Attention has recently been focused on the potential therapeutic role of a number of cytokines in the acceleration of normal wound healing, as well as in the treatment of difficult, chronically non-healing wounds. The cytokines under study include epidermal growth factor (EGF), platelet-derived growth factor (PDGF), the transforming growth factors $\alpha 0$ and $\beta$, and cachectin/tumor necrosis factor-$\alpha$ (TNF). Many cytokines are delivered locally at the wound site by recruited macrophages, which function as the primary scavengers of debris and secrete a large variety of chemotactic, effector, and growth factors.

Accordingly, Fahey et al. supra conducted certain studies with a murine model of wound inflammation to determine the time course of appearance, if any, exhibited by certain cytokines, among them cachectin/TNF, interleukin-1, MIP-1$\alpha$, MIP-1$\beta$ and MIP-2. The murine model utilized by the investigators included an artificial "wound chamber" consisting of a length of perforated silicone tubing containing within its bore a length of polyvinylalcohol sponge. This wound chamber was then inserted into surgically produced subcutaneous pockets in mice. The investigators noted that inflammatory cells rapidly appeared in the recovered wound chamber fluid; and that when the wound chambers were recovered after a few days in situ, fibroblasts had colonized the recovered sponges, collagen and other tissue components had been deposited around the implant and new blood vessels had likewise formed. All of the events noted reflect the natural progression of the inflammatory phase of cutaneous wound healing.

The investigation also revealed that the levels of cachectin/TNF and IL-1 peaked on the first day after the implantation of the wound chamber, and that MIP-1 and MIP-2 were detected on day 3 of implantation only. The data thus suggested that the noted cytokines appear in the early inflammatory response in wound healing.

The novel cytokines, macrophage-inflammatory protein 1 (MIP-1) and macrophage-inflammatory protein 2 (MIP-2), have been previously identified and implicated as mediators of inflammation. MIP-1 is a heparin-binding protein of about 8000 Daltons, which is secreted in large amounts by stimulated macrophages and which migrates as a doublet on sodium dodecyl sulfate-polyacrylamide gel electrophoresis (SDS-PAGE). The two electrophoretic bands were resolved, and the corresponding peptides were partially sequenced independently, as set forth in application Ser. No. 104,287. Complete cDNAs coding for the two peptides were thereafter sequenced, and the translated peptides have been designated MIP-1$\alpha$ and MIP-1$\beta$, as set forth in application Ser. No. 238,937. Purified doublet MIP-1 has been shown to be a potent pyrogen (See also Davatelis, G. et al., "Macrophage Inflammatory Protein-1: A Prostaglandin-independent Endogenous Pyrogen", *Science*, 243:1066-1068, 1989) and to activate neutrophils as shown by enhancing neutrophil chemokinesis and generation of a superoxide burst (See also Wolpe, S. D. et al., "Macrophages Secrete A Novel Heparin-binding Protein With Inflammatory and Neutrophil Chemokinetic Properties", *J. Exp. Med.*, 167:570-582, 1988).

The inflammatory cytokine macrophage-inflammatory protein 2 (MIP-2) was disclosed in co-pending application Ser. No. 240,078. This inflammatory cytokine was found to bind to heparin more avidly than MIP-1 and exhibited the distinguishing characteristics over the former of a molecular weight of approximately 6 kilodaltons, and chemotactic rather than chemokinetic activity for neutrophils. The cytokines MIP-1 (doublet), MIP-1α and MIP-1β and MIP-2 were later determined to exhibit a promoting effect on the colony and cluster formation activities of granulocyte-macrophage progenitor cells (CFU-GM) from the bone marrows of normal mice and humans co-stimulated with suboptimal concentrations of known colony stimulating factors. In co-pending application Ser. No. 377,937, the utility of these cytokines in promoting myeloid blood cell production has been demonstrated.

The exact role that cytokines such as MIP-1, MIP-1α, MIP-1β and MIP-2 play, if any, in the promotion and facilitation of wound healing remains to be determined, and it is to this determination that the present Application is directed.

SUMMARY OF THE INVENTION

In accordance with the present invention, diagnostic and therapeutic protocols are proposed that are predicated in part on the discovery that certain cytokines have been determined to possess a definitive modulating effect upon the progression of wound healing in mammals.

Accordingly, the present invention relates in its broadest aspect to the treatment of wounds as well as various wound healing dysfunctions by the administration of a wound healing modulator comprising a material selected from the group consisting of agents capable of modulating wound healing, binding partners thereto, and the muteins and fragments thereof, wherein the agents have the following characteristics:
(a) capable of modulating colony stimulating factor (CSF)-dependent hematopoiesis;
(b) capable of binding to heparin; and
(c) capable of inducing localized inflammation characterized by polymorphonuclear cell infiltration when administered subcutaneously. The aforenoted agents may also exhibit the capability of binding to heparin at high salt concentrations.

Suitable agents include materials capable of promoting agent production and/or activity, and materials capable of mimicking agent activity, such as homologous agents derived from other cellular sources or from other species. The agent binding partners contemplated by the invention include anti-agent antibodies, receptors for the agents, materials not antibodies that antagonize the production and/or wound healing modulating activity of the agents, binding partners thereto, and other binding partners thereof. The present wound healing modulators may comprise materials that are capable of acting in vivo, and in a further embodiment, may be promoters of wound healing.

Particular agents determined to possess the above characteristics comprise cytokines that possess the activity profiles of the inflammatory cytokines that were disclosed in co-pending application Ser. Nos. 399,971; 377,937; 240,078; and 238,937. These materials are newly discovered isolates of the mediator substance disclosed in U.S. Pat. No. 4,603,106, and comprise proteins that have been purified. In particular, the agents may be selected from the specific previously identified cytokines, MIP-1, MIP-1α and MIP-1β, and MIP-2, and mixtures of these.

MIP-1 comprises two peptides, MIP-1α and MIP-1β and is capable of: modulating CSF-dependent hematopoietic colony and cluster formation; binding to heparin even at high salt concentrations; and inducing localized inflammation when administered subcutaneously.

MIP-2 comprises a single peptide and is capable of: modulating CSF-dependent hematopoietic colony and cluster formation; binding to heparin even at high salt concentrations; and inducing inflammation when administered in vivo.

In a second aspect thereof, the present invention comprises a method for promoting wound healing comprising administering an effective amount of one of the above wound healing modulators individually, or in mixture with each other or formulated as a pharmaceutical composition. More particularly, the modulators contemplated for use in this method comprise those agents and binding partners that act as promoters of wound healing, and extend for example, to homologous agents derived from other cellular sources or from other species, materials capable of promoting agent production and/or activity, and materials capable of mimicking agent activity.

Pharmaceutical compositions may be prepared in accordance with the invention and comprise therapeutically effective amounts of the present wound healing modulators, either alone or in admixture with each other, and a pharmaceutically acceptable diluent or carrier. The modulators may preferably be present in amounts effective to deliver at least 100 ng/cm$^2$ and preferably from about 1 μg/cm$^2$ to about 10 μg/cm$^2$ thereof.

The therapeutic methods of the present invention apply generally to mammals and contemplate veterinary use as well as application to humans. The particular therapeutic protocols will vary accordingly upon the subject of treatment.

In the instance where wound healing may be beneficially monitored, such as to identify suspected disorders affecting wound healing, the present invention contemplates a method for measuring the activity of the wound healing modulators of the present invention. The method comprises retrieving a sample of wound inflammatory fluid, tissue or blood from a patient in which such disorder is suspected, and incubating the sample with a quantity of a wound healing modulator of the present invention bearing an appropriate detectable label. The sample may thereafter be examined to determine whether such aberrant cellular activity is due to a deficiency in wound healing factor presence or activity, and to thereby attempt to isolate and identify the cause of such disorder. The present invention may also extend to appropriate new drug assays and test kits including the wound healing modulators of the present invention.

Accordingly, it is a principal object of the present invention to provide a method for treating wound healing dysfunctions in mammals.

It is a further object of the present invention to provide a method as aforesaid that is applicable to the promotion of wound healing.

It is a yet further object of the present invention to provide pharmaceutical compositions for use in therapeutic methods for treating wound healing dysfunctions and/or promoting wound healing which comprise or are based upon certain wound healing modulators including agents and their binding partner(s).

It is a still further object of the present invention to provide a method for promoting wound healing by the administration of the pharmaceutical composition as aforesaid.

It is a further object of the present invention to provide a method for measuring the activity of the wound healing modulators as aforesaid, that also serves to evaluate possible disorders in wound healing.

Other objects and advantages will become apparent to those skilled in the art from a review of the ensuing description which proceeds with reference to the following illustrative drawings.

DETAILED DESCRIPTION

Figure 1:
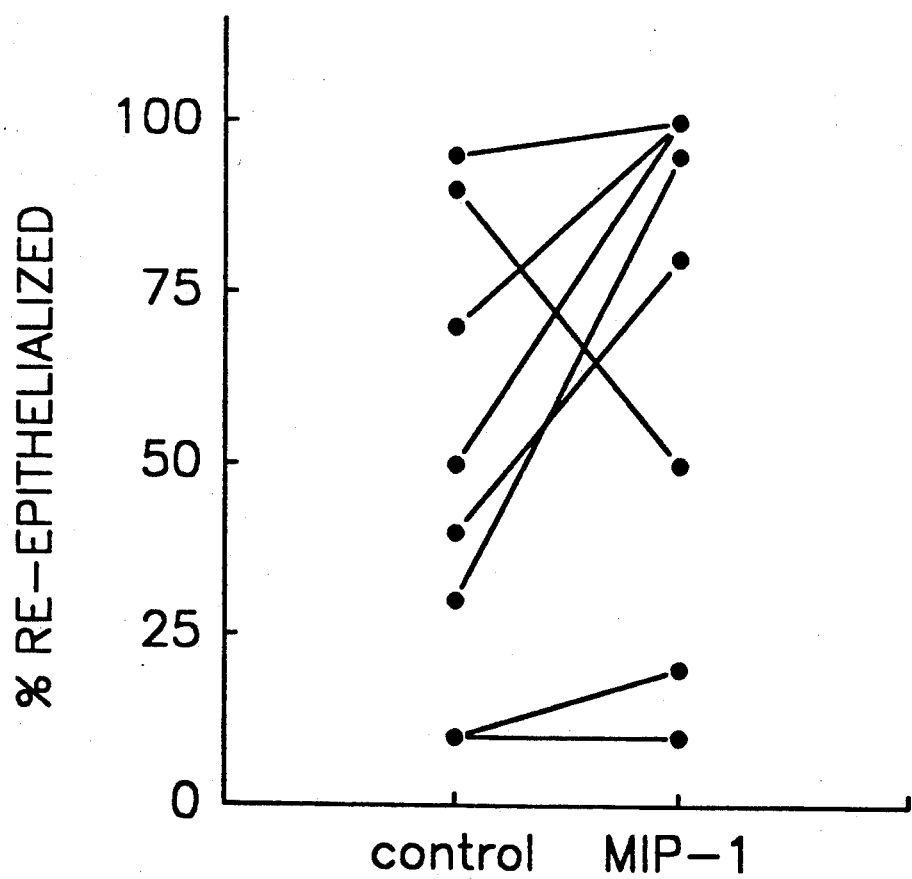
FIG. 1 is a graph depicting a comparison of extent of re-epithelialization between pairs of control LPS-treated and matched MIP-1 (doublet)-treated wounds (N=18 pairs total). Matched wound pairs which received 3 to 10 $\mu$g purified native MIP-1 (doublet) are included (N=8 pairs). Wound pairs in which both the control LPS-treated and MIP-1 (doublet)-treated wounds were 100% re-epithelialized (N=2 pairs) have been omitted, because enhanced re-epithelialization with cytokine treatment could not, by definition, have been detected in test pairs where the control wound fully re-epithelialized. Wound pairs which received 1 or 2 $\mu$g MIP-1 (doublet) did not show a consistent pattern of enhanced or decreased wound healing with cytokine treatment (N=8; one pair showed decreased re-epithelialization, two pairs showed enhanced re-epithelialization, two pairs showed no difference between cytokine- and LPS-treated, and three pairs showed 100% re-epithelialization in both cytokine- and LPS-treated; data not shown).

In accordance with the present invention there may be employed conventional molecular biology, microbiology, and recombinant DNA techniques within the skill of the art. Such techniques are explained fully in the literature. Therefore, if appearing herein, the following terms shall have the definitions set out below.

The term "stimulus" and its plural as used herein are intended to apply to invasive events such as infection, as well as conditions caused by wounding, and to idiopathic or spontaneous states that may for example, originate from cellular or metabolic derangements or other causes.

The terms "wound healing modulator", "agent" and "cytokine" as used throughout the present application and claims refer to protein material having the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of these materials. Also, the terms "wound healing modulator", "agent" and "cytokine" are intended to include within their scope proteins specifically recited herein as well as all substantially homologous analogs and allelic variations.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

An "antibody" is any immunoglobulin, including antibodies and fragments thereof, that binds a specific epitope. The term encompasses, inter alia, polyclonal, monoclonal, and chimeric antibodies, the last mentioned described in further detail in U.S. Pat. Nos. 4,816,397 and 4,816,567.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein in the qualitative sense to mean an amount sufficient to promote the healing of a non-healing wound. Quantitatively, this phrase means an amount sufficient to promote, and preferably accelerate by at least about 10 percent, more preferably by at least 20 percent, a clinically significant change in the rate or extent of wound healing as a result of the administration of the wound healing modulator of the present invention.

In its primary aspect, the present invention concerns methods of diagnosing and treating wound healing dysfunction by resort to the identification and administration of certain modulators of wound healing, including certain agents represented in part by a class of cytokines that are believed to be implicated in the promotion of wound healing.

As indicated earlier, the present invention is in part, the outgrowth of experimentation with the recently identified and purified cytokines whose common properties are that they modulate hematopoietic colony stimulating factor activity, bind to heparin even at high salt concentrations, and induce localized inflammation characterized by polymorphonuclear cell infiltration when administered subcutaneously. The cytokines in object are identified as MIP-1, MIP-1$\alpha$ and MIP-1$\beta$, and MIP-2, and a full exposition of their origins, structures and activity profiles are set forth in commonly assigned parent application Ser. Nos. 399,971; 377,937; 240,078; and 238,937. The disclosures of these applications are incorporated herein by reference.

MIP-1 comprises peptides of inferred sequence. Specifically, MIP-1 is known to comprise two purified peptide components that display the amino acid sequences set forth below as determined in mice.

MIP-1α

ALA PRO TYR GLY ALA ASP THR PRO THR ALA CYS CYS PHE SER
TYR SER ARG LYS ILE PRO ARG GLN PHE ILE VAL ASP TYR PHE
GLU THR SER SER LEU CYS SER GLN PRO GLY VAL ILE PHE LEU
THR LYS ARG ASN ARG GLN ILE CYS ALA ASP SER LYS GLU THR
TRP VAL GLN GLU TYR ILE THR ASP LEU GLU LEU ASN ALA

MIP-1β

ALA PRO MET GLY SER ASP PRO PRO THR SER CYS CYS PHE SER
TYR THR SER ARG GLN LEU HIS ARG SER PHE VAL MET ASP TYR
TYR GLU THR SER SER LEU CYS SER LYS PRO ALA VAL VAL PHE
LEU THR LYS ARG GLY ARG GLN ILE CYS ALA ASN PRO SER GLU
PRO TRP VAL THR GLU TYR MET SER ASP LEU GLU LEU ASN

Likewise, MIP-2 comprises a single purified peptide and displays the mature amino acid sequence set forth below as determined in mice.

MIP-2

ALA VAL VAL ALA SER GLU LEU ARG CYS GLN CYS LEU LYS THR
LEU PRO ARG VAL ASP PHE LYS ASN ILE GLN SER LEU SER VAL
THR PRO PRO GLY PRO HIS CYS ALA GLN THR GLU VAL ILE ALA
THR LEU LYS GLY GLY GLN LYS VAL CYS LEU ASP PRO GLU ALA
PRO LEU VAL GLN LYS ILE ILE GLN LYS ILE LEU ASN LYS GLY
LYS ALA ASN

Naturally, other cell lines or other sources for the development of either the material from which the cytokines are thereafter isolated, the inflammatory cytokines themselves, or other homologous agents exhibiting wound healing modulating activity are contemplated herein and the present invention is accordingly not limited. Thus, alternate means such as by recombinant techniques are contemplated herein in accordance with the present invention and as set forth in the parent applications referenced earlier herein.

The heparin-binding protein MIP-1 has previously been shown to elicit a localized inflammatory response when injected s.c. into footpads of C3H/HeJ mice (Wolpe, S. D. et al., *J. Exp. Med.*, 167, 1988). MIP-1 acts as a prostaglandin-independent endogenous pyrogen when administered to rabbits (Davatelis, G. et al., *Science*, 243, 1989) and is capable of inducing in vitro chemokinesis of human neutrophils and of triggering adherent neutrophils to release hydrogen peroxide (Wolpe, S. D. et al., *J. Exp. Med.*, 167, 1988).

More particularly, the present invention includes methods and compositions for promoting wound healing, as it has been noted that agents possessing the general activity profile of the inflammatory cytokines MIP-1, MIP-1α, MIP-1β, and MIP-2 improve wound healing when applied to wounds.

As discussed earlier, the present invention includes therapeutic methods employing the wound healing modulators identified herein and compositions containing the same for use in such methods. Accordingly, the wound healing modulators of the present invention comprising the agents, their homologs, similarly active drugs, their receptors, their binding partner(s) or other ligands or agents exhibiting either mimicry or antagonism to the agents or control over their production, may be prepared in pharmaceutical compositions, with a suitable carrier and at a strength effective for administration by various means to a patient having a tissue wound or a wound healing disorder or dysfunction, for the treatment thereof.

A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, including delivery in an irrigation fluid used to wash body wound areas, catheterizations and the like. Average quantities of the wound healing modulator may vary and in particular should be based upon the recommendations and prescription of a qualified physician or veterinarian.

In particular, concentrations of the wound healing modulator may range from at least about 100 ng/cm$^2$, and preferably from about 1 µg/cm$^2$ to about 10 µg/cm$^2$ may be used. The exact quantities of the wound healing modulator administered may vary and should be based upon the recommendations and prescription of a qualified physician or veterinarian.

As mentioned earlier, the materials that function as modulators of wound healing extend to the binding partners of the agents defined herein, and particularly include the antibodies, receptors, materials not antibodies to the agents that antagonize the production and/or wound healing modulating activity of the agents and other binding partners thereto. In the instance of certain cytokines, specific antibodies to the cytokines that would antagonise the modulating effect that they exert on wound healing could be identified.

Antibodies, including both polyclonal and monoclonal antibodies, and drugs may also be raised to the agent and may be utilized where appropriate for the purpose of modulating wound healing by a mammalian host. In particular, the agent may be used to produce antibodies to itself in a variety of animals, by known techniques such as the hybridoma technique utilizing, for example, fused mouse spleen lymphocytes and myeloma cells. The resulting antibodies could then be prepared in a suitable pharmaceutical composition and administered to the intended host. The exact quantities, intervals of administration and administrative techniques respecting such pharmaceutical compositions may vary in accordance with those known in the medical arts, and upon the specific instruction of a qualified physician or veterinarian.

Similarly, the agents may bind to particular naturally occurring binding activities including cell associated and soluble receptors to facilitate intracellular transmission of messages relating to wound healing activity, and these binding activities or receptor molecules may be identified as they form complexes with the agents, and thereafter may be isolated and prepared in sufficient quantities to be used in the same fashion as the agents themselves, to modulate wound healing activity. By way of illustration and not limitation, a variety of diverse receptor systems are known, such as the tyrosine kinases and G-protein receptors are already known and operate to transmit messages to the genetic material of the cell to cause corresponding changes in protein synthesis, and the present invention contemplates that these molecules and other functionally similar molecules, may participate in wound healing modulation in accordance herewith.

The present invention also relates to a variety of diagnostic applications, including methods for detecting or investigating disorders or dysfunctions in wound healing by reference to the ability of the present wound healing modulators of the present invention comprising the agents and their binding partners to promote or inhibit wound healing activity. As mentioned earlier, the agents or their binding partners could be appropriately labeled and placed in contact with a sample of wound inflammatory fluid, tissue or blood from a mammal in which the disorder is suspected. Thereafter, the sample could be examined to determine the location and status of the labeled material as well as the general activity of the sample, i.e. whether wound healing activity has increased or decreased.

As indicated earlier, the following examples set forth the details of the investigation and identification of the wound healing promoting activity of the stated inflammatory cytokines. Naturally, the specific materials and techniques set forth hereinafter are exemplary only and may vary, so that the following is presented as illustrative but not restrictive of the present invention.

EXAMPLE 1

Promotion of Wound Healing in vivo by MIP-1, MIP-1α, and MIP-1β

This series of experiments sought to determine whether the cytokines MIP-1, MIP-1α, MIP-1β or MIP-2 were involved in any way in promoting wound healing. Accordingly, MIP-1, MIP-1α, MIP-1β, and MIP-2 were assessed in a standard porcine model of wound healing in response to partial thickness skin injury.

Materials and Methods

Surgical Wounding

The wound healing model used in these studies is a modification of that described by Eaglstein and co-workers ("New Method for Assessing Wound Healing: The Effects of Triamcinolone Acetonide and Polyethylene Film Occlusion," *J. of Invest. Derm.*, 71:382-384, 1978). Young White Yorkshire pigs weighing 10–15 kg were used for all wounding experiments. Anesthesia was induced in the following manner: Pigs received pre-operative medication with Azaperone (1 mg/lb), Atropine (0.04 mg/kg) and Ketamine (10 mg/kg) by i.m. injection. Animals were then taken to the surgical suite, intubated and maintained under Isofluorane inhalation anesthesia and nitrous oxide at 1.5 L/min. The animals were given supplemental oxygen during the procedure and maintained on a warming blanket.

Once adequate anesthesia had been attained, the back and dorsal thorax of the pigs was shaved and prepared with a 70% alcohol solution. Temperature was monitored throughout the operation, and an i.v. line (started after the animal was asleep) was maintained. Depth of anesthesia was monitored by corneal reflexes and withdrawal to painful stimuli. Anesthesia was titrated to maintain an unresponsive state. Partial thickness epidermal wounds were then made with a Padgett dermatome to a depth of 0.015 inches. Wounds were 2×5 cm in area. This type of injury, which removes the epidermis and a zone of the superficial dermis but spares the hair follicles, has been previously shown to be comparable to a second degree burn injury or a donor site for a skin graft. Once all of the wounds had been created (eight pairs of wounds were made, one wound of each pair on each side of the midline), the wounds were treated and dressed. The animals were then allowed to emerge from anesthesia and monitored closely for pain. Pain was treated with Demerol (10 mg/kg i.m.) every 4–6 hours as needed.

Treatment of Wounds

Partial thickness cutaneous wounds were treated in pairs; one wound of each pair was treated with cytokine in vehicle (PBS), the other treated with an amount of bacterial endotoxin (lipopolysaccharide, LPS) in vehicle, where the amount of LPS was the same as the amount of LPS which contaminated the cytokine preparation. Wounds were treated in a pattern of bilateral pairs, whereby every cytokine-treated wound was matched to a contralaterally corresponding LPS-treated wound at the same location on the other side of the midline of the back.

Solutions of purified native MIP-1, purified recombinant MIP-1α, purified recombinant MIP-1β, both purified native and purified recombinant MIP-2, or *E. coli* LPS, were prepared in vehicle from concentrated stocks (below) to the desired final concentrations. A 50 μl drop of cytokine- or LPS-containing vehicle or vehicle alone was applied to each wound, and spread over the wound with the tip of a sterile pipette.

Wounds were individually sealed with a semipermeable dressing: Benzoin was applied as an adhesive to a zone of intact skin surrounding the perimeter of each wound and the wound was sealed with a patch of Opsite applied to cover the wound and extend over and adhere to the zone of Benzoin-treated intact skin surrounding each wound. Opsite-sealed wounds were then covered with a bulky dressing.

Cytokines and Endotoxin

Native MIP-1 (doublet) was purified from culture medium conditioned by LPS-stimulated RAW 264.7 cells according to a protocol modified from Wolpe et al., 1988. Briefly, serum-free culture supernatants from RAW 264.7 cell cultures stimulated with 1 μg of *E. coli* LPS per ml for about 18 hours were pooled, then concentrated and diafiltrated into 20 mM Tris-HCl buffer, pH 8.0, using a hollow fiber concentration system with a 10,000-dalton cutoff (Amicon Corp., Lexington, Mass.). Octyl glucoside was added to the concentrated, diafiltrated supernatant to a final concentration of 1% (wt/vol), and this mixture was fractionated by FPLC anion exchange chromatography (Mono Q 10/10 column from Pharmacia Fine Chemicals, Piscataway, NJ) in an increasing gradient of NaCl.

Fractions containing the MIP-1 (doublet) were identified by SDS-denaturing polyacryamide gel electrophoresis (SDS-PAGE) in gradient slab gels, pooled, and concentrated using an Amicon filtration device equipped with a PM10 membrane. This concentrated material was desalted and exchanged into 0.1M sodium acetate buffer containing 0.2M NaCl, pH 7.8 (Buffer A), using PD10 columns (Pharmacia).

A chelating Superose HR10/2 column (Pharmacia) was precharged with zinc, using a neutral solution of zinc chloride according to the manufacturer's directions, and equilibrated in Buffer A. The concentrated solution of partially purified MIP-1 was loaded and run into this column, and non-binding proteins were washed out in several column volumes of Buffer A. Bound proteins, including MIP-1, were eluted with a 20 ml linearly decreasing pH gradient from 7.8 to 4.0 in Buffer A. MIP-1 containing fractions (identified by SDS-PAGE analysis) were pooled, concentrated in an Amicon filtration device as above, and further fractionated on an FPLC gel filtration column (Superose 12 column from Pharmacia) in 100 mM ammonium acetate buffer. MIP-1 (greater than 95% pure as judged from SDS-PAGE analysis) eluted in the void volume of this column, due to its tendency to form high molecular weight aggregates, especially in this buffer system. Eluate fractions containing MIP-1 were identified (by inspection of SDS-PAGE analyzed aliquots), pooled, and concentrated by centrifugation in Centricon 10 microconcentrator tubes. Protein concentration in this stock of purified native MIP-1 concentrate was estimated using the Bio-Radkit from Sigma according to the manufacturer's instructions with bovine gamma globulin (Sigma) as standard. Aliquots of the purified native MIP-1 concentrate were sterilized by filtration and stored at 4° C. until use.

MIP-1α and MIP-1β were separately produced by the Chiron Corporation, Emeryville, Calif., using recombinant technologies based on proprietary yeast vectors genetically engineered to produce mature MIP-1α and MIP-1β cytokine peptides, Semi-purified MIP-1α and MIP-1β were prepared from crude yeast cell lysates by column chromatography over Mono-S at low pH and were gifts from Chiron Corporation. Applicants further purified recombinant MIP-1α and recombinant MIP-1β from the respective semi-pure preparations by sequential Mono-Q and Superose 12 chromatography steps as described above. Later preparations of recombinant MIP-1α and MIP-1β were additionally purified by reverse phase HPLC by Chiron Corporation and required no further purification before use. Protein concentration and endotoxin content of the purified recombinant MIP-1α and purified recombinant MIP-1β concentrates were estimated as above, and the concentrates were stored at −20° C. until used.

Native murine MIP-2 was purified from culture medium conditioned by LPS-stimulated RAW 264.7 cells according to a protocol modified from Wolpe, S. D., Sherry, B., Juers, D., Davatelis, G., Yurt, R. W., and Cerami, A. Identification and characterization of macrophage inflammatory protein 2 (MIP-2). *Proc. Natl. Acad. Sci. U.S.A.*, 86:612–616, 1989. Briefly, serum-free culture supernatants from RAW 264.7 cell cultures stimulated with 1 μg of *E. coli* LPS per ml for about 18 hours were pooled, then concentrated and diafiltrated into 20 mM Tris-HCl buffer, pH 8.0, using a hollow fiber concentration system with a 10,000-dalton cutoff (Amicon). This material was fractionated over a Mono Q anion exchange column as detailed in Wolpe et al., 1989, and the MIP-2 containing flow-through fraction was concentrated in an Amicon filtration device, dialyzed against 0.05M MES buffer (Calbiochem, La Jolla, Calif.), pH 6.7, and applied to a Mono S 10/10 cation exchange column (Pharmacia) equilibrated in the same buffer. MIP-2 was eluted with an increasing gradient of NaCl in MES buffer, and MIP-2 containing fractions were pooled, and further purified by sequential heparin affinity and gel exclusion chromatography as described in Wolpe et al., 1989. Purity and protein concentration were determined as described for MIP-1, and concentrated stocks of purified MIP-2 were sterilized by filtration and stored at 4° C. until use.

Recombinant MIP-2 was produced by Chiron Corporation using recombinant technologies based on proprietary yeast vectors genetically engineered to produce mature MIP-2 peptide. Purified MIP-2 was prepared from crude yeast cell lysates by affinity chromatography over heparin-Sepharose resin (Pharmacia, prepared according to the manufacturer's instructions) and was a gift from Chiron Corporation.

Because concentrated stocks of purified native cytokines are known to contain contaminating endotoxin (LPS), and endotoxin is a well-known stimulus for cytokine production by macrophages, each cytokine-treated wound was matched to a parallel control wound treated with the same amount of LPS as contaminated the cytokine preparation. Stock endotoxin (LPS W, *E. coli* 0127:B8, Difco Laboratories Inc., Detroit, Mich.) was prepared in PBS according to the supplier's instructions and further diluted as required in PBS just before use in tests of wound healing.

Preparations of purified native MIP-1 (doublet) and of purified native MIP-2 contained different amounts of contaminating endotoxin, but in all cases these native preparations contained about 500 Endotoxin Units per mg of purified cytokine. These concentrations are more than 100-fold higher than concentrations which contaminate the recombinant preparations, which preparations contained less than 5 EU/mg protein.

Dosages

Wounds were treated with cytokine once at the time of wounding at various dosages from 1 to 10 μg cytokine protein per 50 μl vehicle (PBS) per wound. Because wounds measured approximately 2×5 cm, this dosage corresponds to 0.1 to 1 μg cytokine protein per cm² wound area, respectively.

Contralaterally corresponding wounds treated once with LPS in vehicle as controls were treated with a 50 μl application similarly to the vehicle alone-treated wounds, except that the vehicle (PBS) contained *E. coli* LPS at the same concentration as contaminated the matched preparation of cytokine.

Biopsy Technique and Histological Analysis

Biopsies of healing wounds were initially taken on days 3, 4 and 5 after wounding. Preliminary analysis of control wounds revealed that day 4 wounds were best suited to display differences in the rate or degree of healing, and day 4 biopsies were obtained from subsequent tests. Control wounds on day 4 typically show mild residual inflammation and fibroblast activity with persisting ulceration in the sense that epidermal regrowth is still incomplete and portions of the dermis remain exposed. Where epidermis is reforming from the margins of the wound and focally from the hair follicles spared by wounding, there is good granular layer formation with areas of overlying cornified epithelium and little parakeratosis. At this incompletely healed stage, then, a variety of histological characteristics of wound healing are intermediate.

Acceleration or retardation of wound healing is manifest to a trained dermatopathologist by light microscopic comparison of histological sections prepared from biopsies of the healing wounds. Histological sections from wounds in which healing has been accelerated by treatment can be expected to have less remaining ulceration or even complete recoverage by epidermis with good granular layer formation and a more complete overlying cornified layer, and little or no residual fibroblast proliferation or parakeratosis. These histological criteria for completeness of healing can be expected to vary in the other direction if wound healing is retarded by treatment.

To assess the rate and completeness of healing, test pigs were anesthetized as at wounding, wound dressings were removed, and the wounds photographed for gross characterization of healing. When fully anesthetized, test pigs were then overdosed with SleepAway euthanasia solution. Elliptical biopsy samples through the full skin thickness (into the layer of subcutaneous fat) and extending across the full width of the wound and into intact skin on either side were then cut from each wound by hand using a scalpel. Biopsy samples were individually fixed by immersion in 10% buffered formalin in coded containers which did not reveal what treatment the parent wound had received. Coded samples were then routinely processed for light microscopic histological analysis by sectioning at 5 μm, mounting on slides, and staining with hematoxylin and eosin. The biopsies were cut into histological sections in a plane normal (perpendicular) to the surface of the skin, so as to include both the full extent of the wound and a small margin of non-wounded skin at each end of the section.

The degree of wound healing was assessed by measuring the linear extent of re-epithelialization across the full width of the histological sections from the wound biopsy; that is, from the boundary of non-wounded skin on one side of the section to the boundary of non-wounded skin at the other side of the wound. Measurements were taken microscopically, by using a calibrated ocular reticule to measure the linear extent of the total wound, and the linear extent of re-epithelialized wound. The linear extent of re-epithelialized wound was then expressed as a percentage of the linear extent of the total wound, and this percentage was taken as a measurement of the degree of wound healing.

The degree of wound healing was assessed by a skilled dermatopathologist who did not have the code key revealing treatment conditions of the parent wounds. Later, the code was broken, and the degree of wound healing in each cytokine-treated wound was compared to the degree of wound healing in a bilaterally matching wound treated with an amount of E. coli LPS equal to the amount of LPS which contaminated the cytokine preparation to which it was matched.

RESULTS

In pilot experiments, the degree of wound healing was assessed in wounds treated once at the time of wounding with MIP-1 or control LPS and allowed 3, 4, 5, or 7 days to heal. Healing was first qualitatively assessed by a skilled dermatopathologist as follows:

The section taken three days following surgery showed a completely healed epidermis. There is minimal residual fibroblast proliferation in the dermis. The epidermis showed good granular layer formation, and very little residual parakeratosis. The control sections treated with lipopolysaccharide showed slightly less well-healed epidermis, with more dermal inflammation and fibroblast activity; the granular layer did not appear as well-healed.

The tissue taken from four and five days post wounding showed a similar pattern. Those treated one time with MIP-1 showed excellent healing of the wounded area. There is a full granular layer, and minimal residual parakeratosis. There is fibroblast activity present in the dermis; minimal inflammation is associated. On the section taken four days after wounding, ulceration is still present in the control sections. The treated sections are completely healed.

These and other pilot studies indicated that day 4 wounds were particularly well-suited to displaying differences in the rate or extent of wound healing, in that LPS-treated control wounds were usually found to be incompletely re-epithelialized after this period, allowing both enhanced or diminished wound healing to be detected. Therefore, day 4 biopsies were obtained from subsequent tests. Although LPS-treated control wounds averaged about 50% re-epithelialization, the range was from 10 to 100%. Results have been pooled from tests on nine different pigs.

Figure 2:
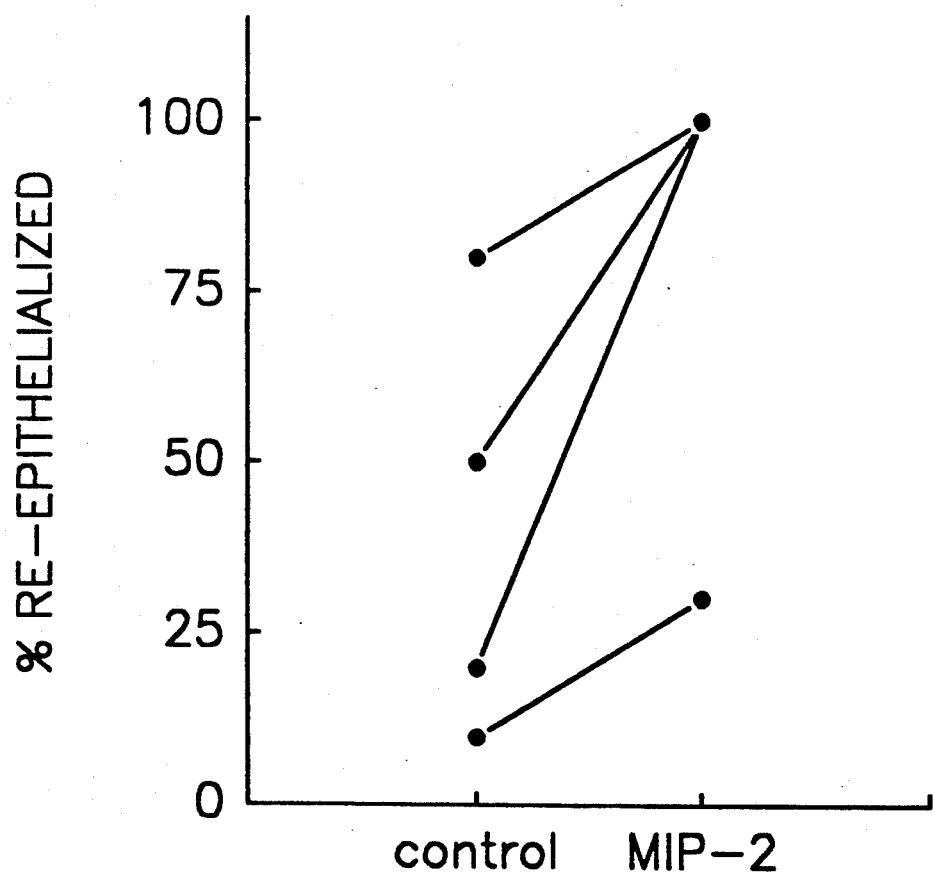
FIG. 2 is a graph depicting a comparison of the extent of re-epithelialization between pairs of control LPS-treated and matched MIP-2 treated wounds (N=4 pairs total). Matched wound pairs which received 1 to 10 $\mu$g purified native MIP-2 are included in the Figure. In this group, no matched pairs showed 100% re-epithelialization in both LPS-treated control and cytokine-treated wounds.
Figure 3:
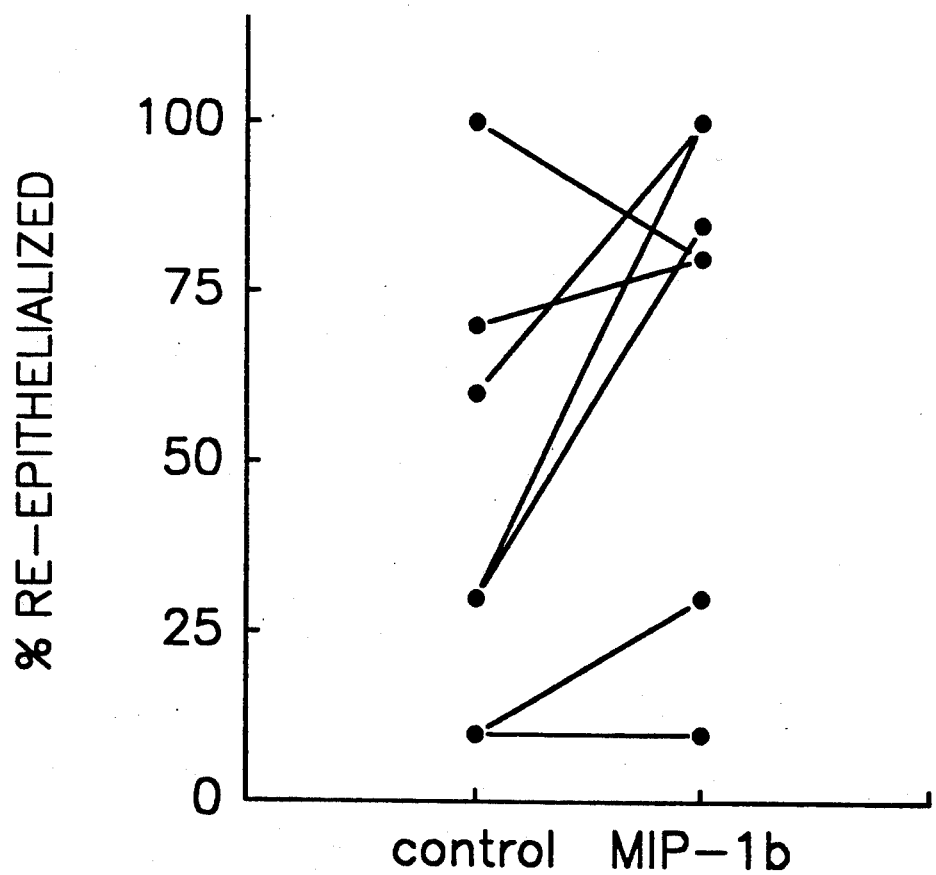
FIG. 3 is a graph showing a comparison of extent of re-epithelialization between pairs of control LPS-treated and matched MIP-1$\beta$-treated wounds (N=8 pairs total). Matched wound pairs which received 1 to 10 $\mu$g purified recombinant MIP-1$\beta$ are included in the figure. In this group, one matched pair showed 100% re-epithelialization in both LPS-treated control and cytokine-treated wounds and that pair has been omitted from the Figure.
Figure 4:
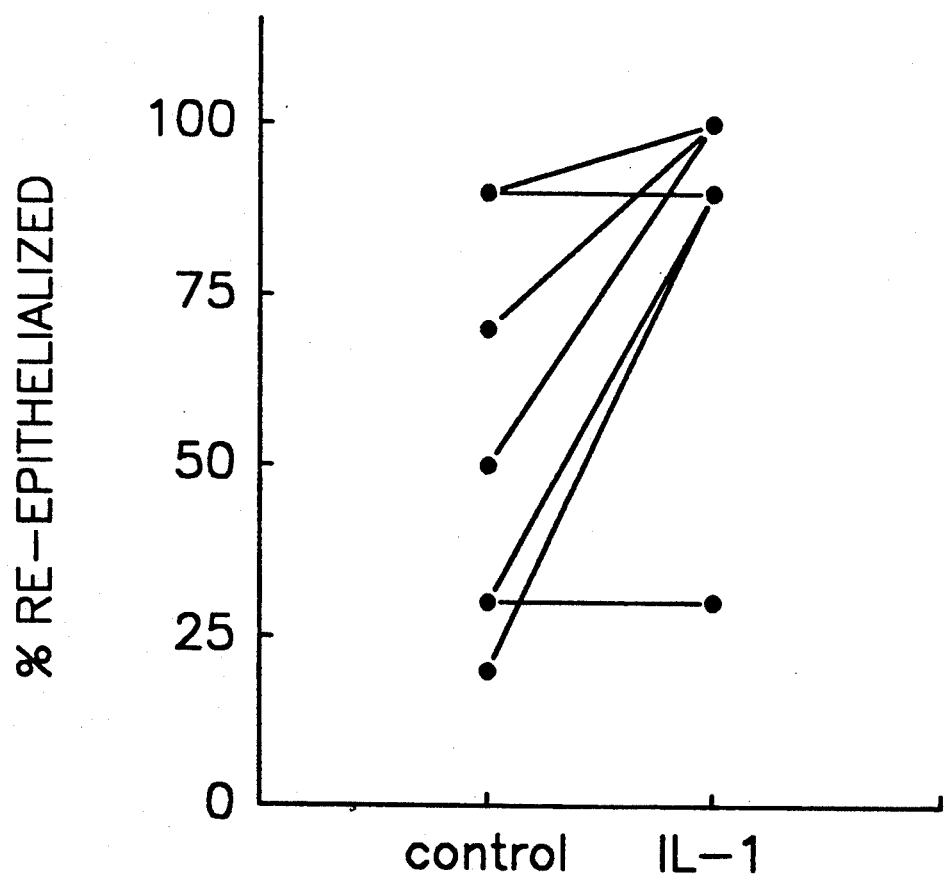
FIG. 4 shows a comparison of extent of re-epithelialization between pairs of control LPS-treated and matched IL-1 treated wounds (N=8 pairs total). Matched wound pairs which received 1 to 10 $\mu$g IL-1 are included in the figure. Wound pairs in which both the control LPS-treated and IL-1-treated wounds were 100% re-epithelialized (N=1 pair) have been omitted from the Figure.

More importantly, the above results demonstrate that the tested cytokines function as promoters of wound healing that may be administered in a controlled setting to assist the wound healing process. Referring to the Figures, wound healing in terms of re-epithelialization was observed with samples treated with the cytokines tested herein. Accordingly, FIG. 1 depicts the results of the application of purified native MIP-1 against a control, and substantial re-epithelialization was evident on samples where from 3 to 10 μg of MIP-1 was applied. Similar significant results were noted in FIG. 2 in the instance of MIP-2 treated samples, where several samples demonstrated virtually 100% re-epithelialization as against LPS controls. The amount of MIP-2 in this instance ranged from 1 to 10 μg purified native MIP-2. Referring to FIG. 3, the same quantity of MIP-1β showed similar improvement, and the data expressed in FIG. 4 demonstrate improved results in the case of IL-1.

As indicated earlier, the agents herein may be formulated for the treatment of animals such as the Yorkshire pigs, as well as with humans, to control the wound healing process, and where desired, to assist in its promotion as evidenced hereinabove.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method of treating wound healing dysfunction in mammals including humans, comprising administering to a mammal a therapeutically effective amount of a wound healing modulator comprising a material selected from the group consisting of an agent for enhancing wound healing, binding partners thereto, and muteins and fragments thereof, wherein said agent possesses the following characteristics:
   (a) capable of modulating colony stimulating factor (CSF)-dependent hematopoiesis;
   (b) capable of binding to heparin; and
   (c) capable of inducing localized inflammation characterized by polymorphonuclear cell infiltration when administered subcutaneously.

2. A method of promoting wound healing in mammals including humans, comprising administering to a mammal a therapeutically effective amount of a wound healing modulator comprising a material selected from the group consisting of an agent for enhancing wound healing, binding partners thereto, and muteins and fragments thereof, wherein said agent possesses the following characteristics:
   (a) capable of modulating colony stimulating factor (CSF)-dependent hematopoiesis;
   (b) capable of binding to heparin; and
   (c) capable of inducing localized inflammation characterized by polymorphonuclear cell infiltration when administered subcutaneously.

3. The method of claims 1 or 2 wherein said agent binds to heparin at high salt concentrations.

4. The method of claims 1 or 2 wherein said wound healing modulator is selected from the group consisting of said agent, homologous agents derived from other cellular sources, homologous agents derived from other species, materials capable of promoting agent production and/or activity, materials capable of mimicking agent activity, muteins and fragments thereof, and mixtures thereof.

5. The method of claim 1 wherein said binding partners to said agent are selected from the group consisting of an anti-agent antibody, a receptor for the agent, a material not antibody to the agent that antagonizes the production and/or wound healing modulating activity of the agent, and mixtures thereof.

6. The method of claims 1 or 2 wherein said agent is a cytokine.

7. The method of claim wherein said cytokine is selected from the group consisting of the inflammatory cytokines MIP-1, MIP-1α, MIP-1β and MIP-2, and mixtures thereof.

8. The method of claim 6 wherein said cytokine is selected from protein homologs of murine MIP-1, MIP-1α MIP-1β, and MIP-2 and mixtures thereof as isolated from other mammalian species, including human.

9. The method of claim 1 wherein said wound healing modulator is capable of acting in vivo.

10. The method of claims 1, 2, 5 or 9, wherein said agent is derived from cells which are produced by recombinant DNA technologies.

11. The method of claim 3 wherein said agent is derived from cells which are produced by recombinant DNA technologies.

12. The method of claim 4 wherein said agent is derived from cells which are produced by recombinant DNA technologies.

13. The method of claim 6 wherein said agent is derived from cells which are produced by recombinant DNA technologies.

14. The method of claim 7 wherein said agent is derived from cells which are produced by recombinant DNA technologies.

15. The method of claim 1 wherein said agent is administered in a concentration of at least about 100 ng/cm² of wound area.

16. The method of claim 1 wherein said agent is administered in a concentration of from about 1 μg to about 10 μg/cm² of wound area.

* * * * *